United States Patent [19]
Hashemi et al.

[11] Patent Number: 5,525,138
[45] Date of Patent: *Jun. 11, 1996

[54] DETERMINATION OF TENSILE MEMBRANE STRESS AND COMPRESSIVE LAYER THICKNESS IN TEMPERED GLASS USING A $CO_2$ LASER BEAM

[75] Inventors: Amin H. Hashemi, Farmington Hills; David N. Heilman, Monroe, both of Mich.

[73] Assignee: Ford Motor Company, Dearborn, Mich.

[ * ] Notice: The term of this patent shall not extend beyond the expiration date of Pat. No. 5,254,149

[21] Appl. No.: 249,101

[22] Filed: May 26, 1994

[51] Int. Cl.⁶ .................................. C03B 32/00
[52] U.S. Cl. ............................. 65/29.18; 73/760
[58] Field of Search ............... 65/29.18; 73/760, 73/788, 799; 219/121.67, 121.68, 121.69

[56] References Cited

U.S. PATENT DOCUMENTS

| | | | |
|---|---|---|---|
| 3,543,979 | 12/1970 | Grove et al. | 225/2 |
| 3,808,439 | 4/1974 | Remois | 250/334 |
| 3,811,775 | 5/1974 | Abu-Saud | 356/35 |
| 4,655,589 | 4/1987 | Cestaro et al. | 356/35 |
| 4,697,082 | 9/1987 | Bartelsen | 250/341 |
| 5,254,149 | 10/1993 | Hashemi et al. | 65/29.18 |

*Primary Examiner*—Donald E. Czaja
*Assistant Examiner*—Sean Vincent
*Attorney, Agent, or Firm*—Lorraine S. Melotik; Roger L. May

[57] ABSTRACT

A determination of the temper quality of a tempered glass sheet is made which includes determining the percentages of the thickness of a tempered glass sheet which are in compression as well as the sheet's tensile membrane stress. The process uses a $CO_2$ laser beam, either on a painted or unpainted glass sheet, to shatter the glass sheet and then comparing the number of pulses required for the glass sheet to shatter to a correspondence, e.g., a graph, of tensile membrane stress v. compression layer thickness as a % of the total thickness of the glass sheet.

10 Claims, 1 Drawing Sheet

DETERMINATION OF TENSILE MEMBRANE STRESS AND COMPRESSIVE LAYER THICKNESS IN TEMPERED GLASS USING A CO₂ LASER BEAM

FIELD OF THE INVENTION

This invention is directed a method for determining the percentages of the thickness of a tempered glass sheet which are in compression as well as the sheet's tensile membrane stress using a $CO_2$ laser beam, either on a painted or unpainted glass sheet.

BACKGROUND OF THE INVENTION

It is generally known in the art of manufacturing automotive glazings that to form a glass sheet templet into suitable shapes, as e.g, a backlite, the glass sheet templet is first heated to a temperature above its plastic set temperature, usually about 1200° F., then shaped to a desired curvature by either gravity forming or press bending the hot glass, and thereafter tempered by directing streams of a tempering fluid, usually moist air, against the major surfaces thereof. It is well-known that ceramic materials are much stronger in compression than in tension. Therefore, "tempered" glass is typically used for vehicle glazings, architectural uses such as glass doors, and other high-strength-requirement applications.

During tempering, residual compressive stresses are intentionally induced in the shaped glass sheet. The major surface regions of the glass sheet contract because of the drop in temperature as a result of convective heat transfer to the cooling air. Thus, the major surface regions of the glass sheet become rigid, while the central portion of the glass sheet remains hot and can adjust its dimensions to the surface region contractions. When the central region of the glass sheet cools and contracts slightly at a later time, compressive stresses are produced in the outer major surface regions of the glass sheet.

A constant cooling rate applied to both major surfaces of the shaped glass sheet, resulting from an identical flow of constant-temperature cooling air to both major surfaces, theoretically would produce a parabolic stress distribution when measured normal to the major surfaces of the glass sheet.

Tempered glass is particularly useful for high-strength applications because the exposed surfaces of the tempered glass sheet are under residual compressive stress. Glass failure usually occurs from an applied tensile (rather than compressive) stress. Since failure in a tempered glass sheet almost always is initiated at one of its major surfaces, e.g., by striking the tempered glass sheet, any applied stress must first overcome the residual compression near the surface of the tempered glass sheet before that region is brought into tension such that failure may occur.

During tempering, it is known to support the shaped glass sheet on a support ring, comprising a rigid structure conforming generally in outline and elevation to the underside peripheral marginal surface of the shaped glass sheet. During the tempering operation, the blasts of tempering fluid rapidly cool the major surfaces of the formed glass sheet in all areas, except those areas near points of contact between the tempering support ring and the underside peripheral marginal surface of the glass sheet. In those areas, cooling is retarded due to the restricted flow of tempering fluid caused by interference with the tempering support ring. As discussed above, after tempering the outermost layers of the tempered glass sheet are in compression while the central layer between the compression layers is in tension, however, those layers of the ultimately produced tempered glass sheet may be stressed in compression/tension in other than optimal numerical amounts and the thickness of the compression layers may be less than optimal for proper tempering strength.

Moreover, other variables in the tempering process can result in poor quality and nonuniform tempering, wherein the configuration of the actual stress (distribution numerical value and thickness of the tension and compression layer) measured across the thickness of the glass sheet at any point along the surface of the tempered glass sheet varies markedly from an idealized parabola. Such a stress imbalance and less than desirable thickness of the compression layers may lead to spontaneous breakage of the tempered glass sheet. Clearly, it is important to be able to modify the tempering conditions as necessary to produce an optimally tempered glass sheet. In order to be able to do this, it is necessary to be able to accurately and conveniently measure the value of the tensile stress in the glass and the thickness of the various layers. It would be desirable to devise such a method for determining these parameters. One process for determining the temper quality has been described in U.S. Pat. No. 5,254,149 to Hashemi et al. which is commonly assigned with the present invention. It teaches a process which involves repeatedly scoring a major surface of a tempered glass sheet with a laser beam until the tempered glass sheet shatters. The patent discloses determining temper quality by comparison between the scoring required to shatter that tempered glass sheet and that required to shatter another tempered glass sheet of desirable quality.

Unexpectedly, we have found that when glass is tempered optimal strength is induced when certain percentages of the thickness of the tempered glass sheet are respectively in compressive stress and in tensile stress. In addition, we have found that proper tempering and hence strength of the tempered glass product are related to an optimal magnitude of the tensile stress, so that there exists a correlation between the compression layer thickness (%) and tension layer stress in properly tempered glass. Prior to this invention, technology has not been suitably capable of determining the thickness of the compression layer (%) as a function of the values of tensile membrane stress in the tempered glass. This invention is capable of determining both, even in glass having a paint on one of its surfaces. Automotive glazing often include a painted portion on the outer areas of such glazings.

SUMMARY OF THE INVENTION

According to the present invention, there surprisingly has been discovered a process for determining temper quality particularly comprising the percentage of the thickness of a tempered glass sheet in compressive stress and the value of the tensile stress. The process comprises the steps of:

A) penetrating a major surface of a tempered glass sheet with pulses of a laser beam generated by a $CO_2$ laser having (a) a power between 5.0 and 200 watts, (b) a pulse length between about 0.1 and 1.0 msec, and (c) pulse interval between about 1 and 10 seconds until the tempered glass sheet shatters; and B) comparing the number of pulses required for the tempered glass sheet to shatter to data developed which comprises a correspondence of tensile membrane stress v. compressive layer thickness as a percentage of the total thickness of sample tempered glass which has the same thickness and composition as the tempered glass sheet.

The process of the present invention is particularly well-suited for determining the temper quality in a tempered glass sheet, such as automotive glass, which information can then be used as a quality control tool for modifying the operating conditions of the tempering process. This temper quality determined according to the present invention process includes the tensile membrane stress and the percentage of the thickness of the tempered glass attributable to each of the compression layers and the tension layers, even for painted glass sheets.

BRIEF DESCRIPTIONS OF THE DRAWINGS

DETAILED DESCRIPTION OF THE PREFERRED EMBODIMENTS

Figure 1:
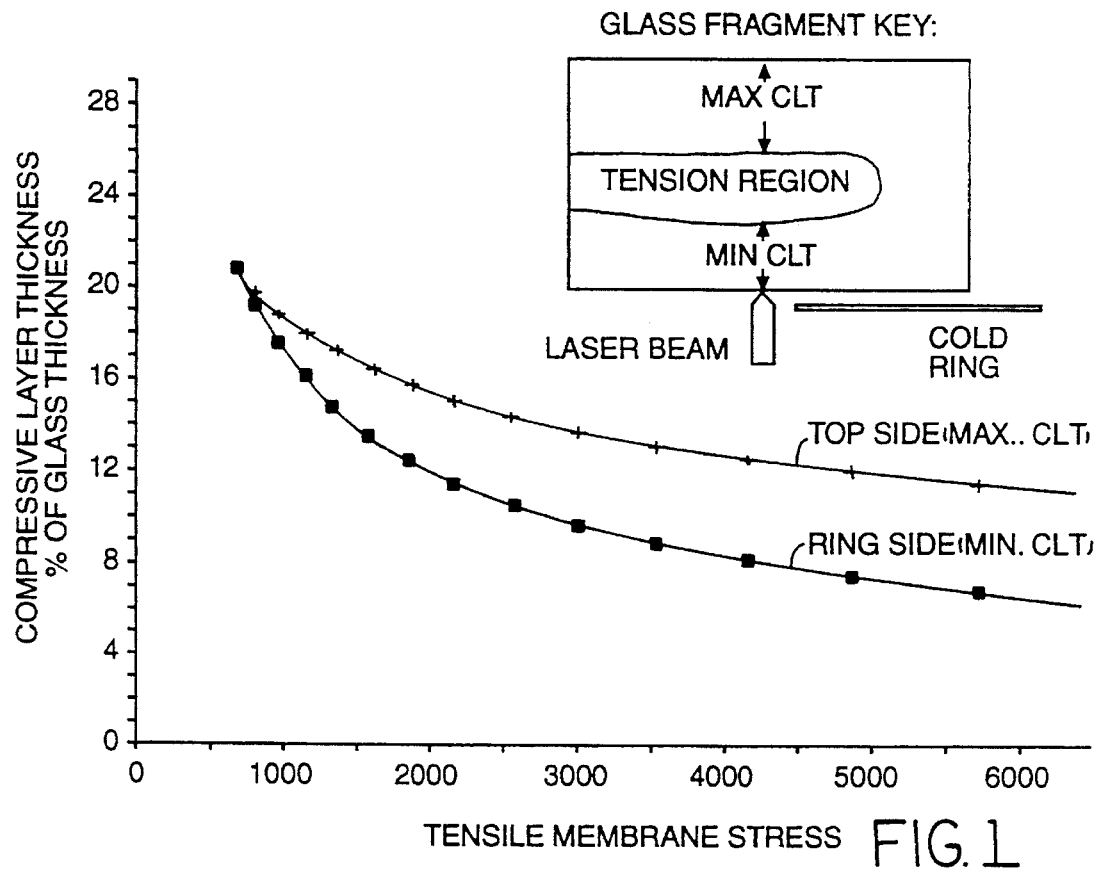
FIG. 1 is a graph according to an embodiment of the invention process which depicts compression layer thickness (as a % of total glass thickness) v. tensile membrane stress.

While poor temper quality is determined by several factors, we have found critical factors to be particularly low compression layer thicknesses of one or both compression layers and/or particularly high tensile membrane stress values, the particular parameters of which are related to the glass composition and the thickness of the tempered glass sheet. The present invention allows a quantitative measurement of the tensile stress induced in the central layer of the tempered glass sheet as well as the thickness of the two outermost layers which are under compressive stress, in the peripheral and other areas of the tempered glass sheet. We have found that by corresponding such measurements, e.g., as by plotting such measurements on a graph, optimal thickness for the compression layers as well as tensile stress can be determined for the particular tempered glass sheet.

The present invention is directed to a process for determining the quality of temper of a tempered glass sheet. According to the invention process, a major surface of the tempered glass sheet is subjected to particularly defined laser beam pulses from a $CO_2$ laser, preferably a circular $CO_2$ laser, until the beam penetrates sufficiently through the thickness of the tempered glass and the glass shatters. To carry out the process of the invention, a major surface of the tempered glass sheet (top or bottom) is subjected to pulses from the $CO_2$ laser, which is preferably a circular $CO_2$ laser. The non-subjected side of the tempered glass sheet may be covered with paint. The laser beam is set at a predetermined energy level between 5 and 200 watts, preferably between about 90 and 120 watts, most preferably about 105 watts. $CO_2$ lasers are well-known in the art, and therefore will not be discussed in detail.

The $CO_2$ laser used to shatter the tempered glass sheet being evaluated according to the present invention (as well as the glass samples discussed below for developing the comparative data) can be one controllable by a computer, as would be appreciated by one skilled in the are in view of the present disclosure, so that a subroutine can be programmed for the laser. For example, one particularly preferred subroutine program for the laser consists of: pulse length—0.5 msec, laser power—105 watts, and pulse interval—4 seconds (correlated with a glass thickness of about 3.8 mm). A gas purge can be carried out if desired, using e.g., oxygen or helium, for any length of time, e.g., 8 seconds or 2 seconds between pulses. The gas purge is desirably used to anneal the glass between pulses to prevent premature failure. As discussed above, the number of pulses initiated by the laser is counted and is generally recorded as by a computer, up to and including the total number of pulses required to shatter the glass (sheet or samples). It is contemplated that the laser output energy may remain constant during the penetration of the tempered glass sheet and this same energy output may be used in testing another area of the temper glass sheet for temper quality. On the other hand, the laser output energy may be varied during the test on one area or between different test areas of the tempered glass sheet. It is preferably for simplicity in correlating the number of pulses required to shatter the tempered glass sheet with the plots developed for determining temper quality to use a constant output energy as would be appreciated by those skilled in the art in view of the present disclosure. As will be appreciated, the present invention can be used to determine the tensile membrane stress at any location across the surface of the tempered glass sheet.

The surface of the tempered glass sheet is penetrated by the laser beam upon being subjected to the continuing pulses of the laser beam, the laser preferably impinging the glass perpendicular to the glass surface. By penetration is meant a process whereby a small amount of the glass is obliterated by the laser energy. Thus, a bore increasingly penetrates the compression layer near a major surface of the tempered glass sheet during each penetration by a laser pulse. While not wishing to be bound by any particular theory regarding the mechanism by which the pulses of the laser beam in of the present invention cause the tempered glass sheet to shatter, it is believed that the laser beam penetration (boring) into the tempered glass causes the glass sheet to shatter spontaneously when the bore has penetrated through the compression layer of the tempered glass sheet to the interface between the compression and tension layer.

The inventive process requires that the surface of the tempered glass sheet be penetrated by the pulses of the laser beam until the tempered glass sheet shatters. The invention process then requires comparing the number of pulses required for the tempered glass sheet to shatter to data developed which comprises a plot of tensile membrane stress v. compressive layer thickness as a % of the total thickness of the tempered glass sheet.

The data developed to correlate the number of laser beam pulses required to shatter the tempered glass sheet with (1) the % thickness of the compression layers and tension layers and (2) the tensile stress is developed by means of a scheme, an embodiment of which is now described. Samples of tempered glass of the same composition and thickness as the tempered glass sheet to be evaluated for temper properties according to the present invention are provided. The stress imbalances (i.e., the total of the tensile and compressive stresses across the total glass thickness) of such samples of tempered glass having various such imbalances and thickness are measured as by means of instruments used in the industry to measure the stress imbalance in glass sheets. Exemplary of such instruments are edge stress devices as that manufactured by Strain Optics Technology or other devices like quartz wedge meters. Since these operate on the principle of light passing through the tempered glass, the glass samples may not include a paint thereon. Still other instruments for measuring stress imbalance can be employed and are well known to those skilled in the art. In order to assemble plots to determine temper quality according to the present invention, stress imbalance tests are performed on the glass samples having a variety of stress imbalances, i.e., from about 900 to 8100 psi. The difference in stress imbalance can be created by subjecting the glass samples to different tempering process parameters. The various samples having these different stress imbalances are then subjected to laser pulses until each shatters, the pulses (and parameters of the laser) being recorded. The laser parameter may be those described above for determining the temper quality of the tempered glass sheet according to the invention process.

Alternately, a single glass sheet sample could be used to develop the comparison data, the sample sheet having regions (as may be viewed through a polariscope) with island colors such as: yellow, orange, red, green, purple, or blue which identify areas with a variety of different and potentially undesirable high tensile membrane stress and low compression layer thickness. As mentioned above, to develop this comparison data the sample glass sheet would have the same thickness and composition as that tempered glass sheet to be evaluated for temper quality according to the method of this invention. These regions can be located on the sample glass sheet using a locating computer and then their corresponding information as to stress imbalance in each of these areas determined by the instruments discussed above. Such instruments are often capable of storing such information as would be desirable. These regions would subsequently be subjected to the pulses of the laser till the area shatters and such information is recorded, conveniently by a computer, along with region colors. Again, desirably the same laser parameters as to power, pulse length, and pulse interval would be used as in evaluating the tempered glass sheet for temper quality.

In order to interpret this data obtained from the samples, it is desirable to correspond the compression layer thickness (as % of glass thickness) with tensile membrane stress, as by plotting such information, an embodiment of which is shown in FIG. 1. The correspondence, as e.g., in a plot of compression layer thickness v. tensile membrane stress, employed in the present invention process need not be one that is in tangible form but can be that stored in the memory of a computer. The criticality lies in correlating the compression layer thickness with the corresponding tensile membrane stress for a glass composition and thickness, as developed, e.g., by means of the scheme described above. However, it is desirably available in tangible form (on paper) so that it can be most conveniently used by practioners employing this invention process in making determinations as to the temper quality of the glass sheet and hence whether that glass sheet is desirable for use. Such is also the case with the other plots mentioned below. Hence, plots are referred to in the following paragraphs merely as exemplary of such correspondence.

Figure 2:
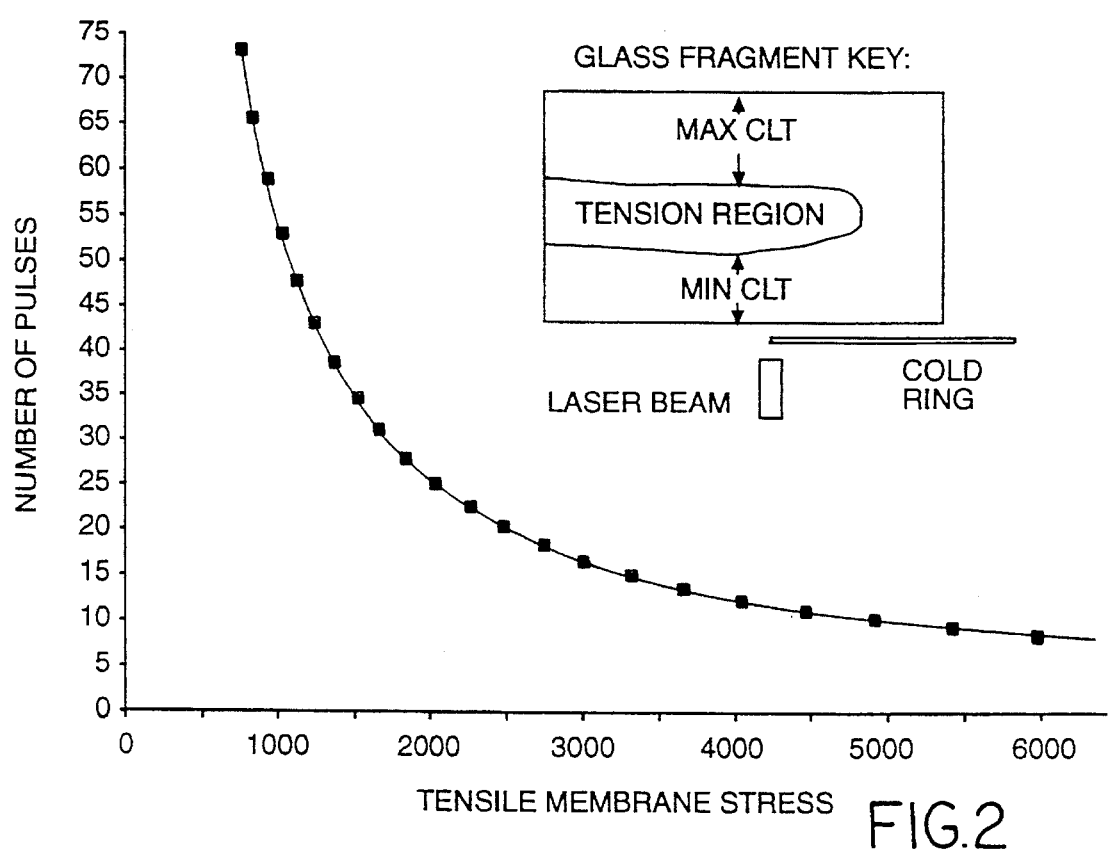
FIG. 2 is a graph according to an embodiment of the invention process which shows the number of pulses required for shatter of a sample of tempered glass v. tensile membrane stress.

In order to be able to develop a plot as shown in FIG. 1, first a plot would be made of pulses required for shatter v. tensile membrane stress in the corresponding area of the glass, an embodiment of this plot being shown in FIG. 2. Using a conversion program, one is able to correlate the tensile stress of the inner tension layer with the number of corresponding pulses till shatter. A second plot (not shown) can similarly be generated which shows the pulses required till shatter (for an area of the sample) v. the corresponding % thickness of the compression layer (for that area), the % thickness of the compression layer being determined as by, e.g., a calibrated microscope. For convenience, such tabulated data could be stored in the library of a computer program (e.g., it may be the one desirably used to control the functioning of the $CO_2$ laser). Subsequently, the % compression layer thickness v. tensile membrane stress plot (as in FIG. 1) could be generated.

Thereafter, in order to carry out a determination of tensile membrane stress and % compression layer thickness according to the present invention process, a piece of tempered glass sheet of the same composition and thickness (3.8 mm in this embodiment) used in generating the plot could be subjected to pulses from a $CO_2$ laser. As would be apparent to those skilled in the art in view of the present disclosure, the number of pulses could be translated to tensile membrane stress from FIG. 2, and then the % compression layer thickness could be read from FIG. 1. From FIG. 1, it can be seen that the optimal % compression layer thickness is about 18–20% of the total glass thickness. Hence, substantially lower compression layer % thicknesses, e.g., 2–6% of total glass thickness comprising the compression layer, would be indicative of a suggestion to vary the tempering process so as to increase the compression layer. As would be apparent to those skilled in the art in view of the present disclosure, for other sample thicknesses of glass and/or composition, similar plots could be generated and used to determine the % compression layer thickness and tensile stress as related to the number of pulses needed to shatter the tempered glass sheet being evaluated. Once the plots are generated from the samples, e.g., those of FIGS. 1 and 2, it is only necessary to employ the present invention process to determine the properties of % compression layer thickness and tensile stress of a tempered glass sheet having the same thickness and composition as that used to generate the plots. As should be apparent in view of the present disclosure, the values as reflected in the plots made from the samples of tempered glass as described above would also apply to the tempered glass sheet being evaluated according to the present invention since the glass composition and thickness used to generate the plots are the same as the glass composition and thickness of the tempered glass sheet.

As indicated above, we have found that optimally for a particular glass composition of a 3.8 mm thickness, the outer glass compression layers should each most desirably comprise at about 18–20% of the total thickness of the glass, and/or the inner layer should be in tension of a magnitude of optimally less than about 1000–2000 psi. Since about 40% of the total glass thickness is desirably in compression, about 60% of the glass is most optimally in tensile stress. Least desirable temper quality is shown by the combination of low compression layer thickness (approximately 8–10% of the total glass thickness and lower) and high tension (38004 psi–8200 psi and greater), which according to the invention embodiment described above is shown by tempered glass which shatters when subjected to 10 laser pulses or less. Utilizing this knowledge, the tempering conditions or tempering support ring materials and configuration could be modified accordingly, to produce a tempered glass sheet of high quality.

EXAMPLE

The regions of island colors are identified in a sample tempered piece of glass sheet (yellow, orange, red, green, purple, or blue) representing high tensile membrane stress and low compressive layer thickness. The tensile stress of such regions is measured and stored in a edge stress meter. The identified regions are penetrated with a $CO_2$ laser beam controlled by a laser machining subroutine program consisting of: pulse length (0.5 sec), laser power (105 watts), pulse interval (4 sec), with a helium purge for two seconds between pulses. The thickness of the glass is 3.8 mm. The number of pulses to shatter is recorderd in the memory of a computer. Next plots are made of pulses as a function of measured tensile membrane stress values and of pulses as a function of measured compressive layer thickness for the corresponding region as measured under a calibrated microscope. The last two plots are used to plot compressive layer thickness as a function of tensile membrane stress. All of the data developed is desirably stored in the library of the program. A 3.8 mm tempered glass sheet, which has a layer of paint on one side, is subjected on the opposite side to a laser beam using same parameters (power, duration, etc.) as is used for the sample until the sheet shatters. The laser machine with a subroutine program compares the pulses till shatter for the tempered glass sheet with that of the tabulated/plotted data for the samples and indicates rejection of a tempered glass sheet having greater than optimal tensile membrane stress values and/or less than optimal compressive layer thickness values, both having been determined from the calculated/corresponded (e.g., plotted) data.

While the parameters of optimally tempered glass sheet for one composition used in the description above are given, the invention is not meant to be so limited. Such numbers may vary and still be considered to be of proper temper. The optimal % thickness and tension for other thicknesses/ compositions of glass may vary from those described in the example above and could be similarly determined as would be apparent to those skilled in the art in view of the present disclosure. In this invention, the tempered glass sheet need not be a flat glass sheet but may also include curved glass sheet material. As is know to those skilled in the art, tensile membrane stress and stress imbalance are considered equivalent expressions in the art and are often used interchangeably.

From the foregoing description, one of ordinary skill in the art can easily ascertain the essential characteristics of this invention, and without departing from the spirit and scope thereof, can make various changes and modification to the invention to adapt it to various usages and conditions.

We claim:

1. A process for determining the percentage of the total thickness of a tempered glass sheet in compressive stress and the tensile stress of the tempered glass sheet, comprising the steps of:

A) penetrating a major surface of the tempered glass sheet with a number of pulses of a laser beam generated by a circular $CO_2$ laser having (a) a power between 5.0 and 200 watts, (b) a pulse length between about 0.1 and 1.0 msec, and (c) pulse interval between about 1 and 10 seconds until said glass sheet shatters; and B) comparing said number of pulses required for said tempered glass sheet to shatter to data which comprises said number of pulses as well as a correspondence of tensile membrane stress v. compression layer thickness as a % of the total thickness of samples of tempered glass having the same thickness and composition as said tempered glass sheet.

2. The process according to claim 1, wherein said process comprises corresponding said compression layer thickness v. the number of pulses to shatter said samples of tempered glass of the same thickness and composition as said tempered glass sheet.

3. The process according to claim 1, wherein said process comprises corresponding said tensile membrane stress v. the number of pulses to shatter said samples of tempered glass of the same thickness and composition as said tempered glass sheet.

4. The process according to claim 1, wherein at least a portion of one side of said tempered glass sheet has a coat of paint thereon.

5. The process according to claim 1, wherein said correspondence is provided in a graph which plots said tensile membrane stress v. said compression layer thickness.

6. A process for determining the percentage of the total thickness of a tempered glass sheet in compressive stress and the tensile stress of the tempered glass sheet, comprising the steps of:

A) penetrating a major surface of the tempered glass sheet of a thickness of about 3.8 mm with a number of pulses of a laser beam generated by a circular $CO_2$ laser having (a) a power of 105 watts, (b) a pulse length of 0.5 msec, and (c) pulse interval of about 4 seconds until said tempered glass sheet shatters; and B) comparing said number of pulses required for said tempered glass sheet to shatter to data which comprises said numbers of pluses as well as a correspondence of tensile membrane stress v. compression layer thickness as a % of the total thickness of samples of tempered glass of the same thickness and composition as said tempered glass sheet.

7. The process according to claim 6, wherein at least a portion of one side of said tempered glass sheet has a layer of paint thereon.

8. The process according to claim 6, wherein said process comprises corresponding said compression layer thickness v. the number of pulses required to shatter said samples of tempered glass of the same thickness and composition as said tempered glass sheet.

9. The process according to claim 6, wherein said process comprises corresponding said tensile membrane stress v. the number of pulses required to shatter said samples of tempered glass of the same thickness and composition as said tempered glass sheet.

10. The process according to claim 6, wherein said correspondence is provided in a graph which plots said tensile membrane stress v. said compression layer thickness.

* * * * *